United States Patent [19]

Magruder et al.

[11] Patent Number: 4,751,071

[45] Date of Patent: Jun. 14, 1988

[54] COMPOSITION COMPRISING SALBUTAMOL

[75] Inventors: Paul R. Magruder, Palo Alto; Brian Barclay, Menlo Park; Patrick S. L. Wong, Hayward; Felix Theeuwes, Los Altos, all of Calif.

[73] Assignee: Alza Corporation, Palo Alto, Calif.

[21] Appl. No.: 1,135

[22] Filed: Jan. 7, 1987

Related U.S. Application Data

[62] Division of Ser. No. 556,985, Dec. 1, 1983, abandoned.

[51] Int. Cl.$^4$ .................................................. A61J 3/07
[52] U.S. Cl. ...................................... 424/467; 604/892; 604/893; 604/896; 564/360; 260/500.5 H; 514/649
[58] Field of Search ..................... 424/16, 19; 604/892, 604/893, 896; 544/162; 564/360; 260/500.5 H; 514/649

[56] References Cited

U.S. PATENT DOCUMENTS

| | | | |
|---|---|---|---|
| 3,644,353 | 2/1972 | Lunts et al. | 260/500.5 H |
| 4,077,407 | 3/1978 | Theeuwes et al. | 128/260 |
| 4,111,202 | 9/1978 | Theeuwes | 128/260 |
| 4,200,098 | 4/1980 | Ayer et al. | 128/260 |
| 4,285,987 | 8/1981 | Ayer et al. | 427/3 |
| 4,522,625 | 6/1985 | Edgren | 424/19 |
| 4,539,198 | 9/1985 | Powell et al. | 424/19 |

FOREIGN PATENT DOCUMENTS 1453034 10/1976 United Kingdom.

OTHER PUBLICATIONS

"The Merck Index" Merck and Co., N.J. (ninth ed.) (1976) p. 216.
65455k Chem. Abstracts, vol. 83, 1975; p. 445.

Primary Examiner—Joseph L. Schofer
Assistant Examiner—F. M. Teskin
Attorney, Agent, or Firm—Paul L. Sabatine; Edward L. Mandell; Shelley G. Precivale

[57] ABSTRACT

An osmotic delivery system is disclosed for delivering a useful agent at a controlled and constant rate modulated by a pulsed delivery of the useful agent to an environment of use.

1 Claim, 6 Drawing Sheets

DRUG SOLUBILITY, OSMOTIC PRESSURE, AND DRIVING FORCE DATA OF SATURATED SALBUTAMOL HEMISULPHATE IN VARIOUS CONCENTRATIONS OF NaCl IN H$_2$O @ 37°C

| NaCl (% OF SATURATION) | $S_d$ (mg/ml SALBUTAMOL HEMI SO$_4$) | $S_T$ (mg/ml) | $\pi$ (atm) | $\pi \cdot S_d/100$ |
|---|---|---|---|---|
| 0 | 270 | 273 | 30 | 81 |
| 14.3 | 281 | 336 | 85 | 239 |
| 26.3 | 280 | 370 | 134 | 375 |
| 38.4 | 302 | 426 | 207 | 625 |
| 47.7 | 235 | 368 | 220 | 517 |
| 62.8 | 103 | 318 | 227 | 234 |
| 85.2 | 42 | 317 | 297 | 125 |
| 100.0 | 11 | 340 | 393 | 43 |

$\pi$ = OSMOTIC PRESSURE GENERATED FROM THE MIXTURE OF SALBUTAMOL HEMISULPHATE AND NaCl SOLUTION

DRUG SOLUBILITY, OSMOTIC PRESSURE, AND DRIVING FORCE DATA OF SATURATED SALBUTAMOL HEMISULPHATE IN VARIOUS CONCENTRATIONS OF NaCl IN $H_2O$ @ 37°C

| NaCl (% OF SATURATION) | $S_d$ (mg/ml SALBUTAMOL HEMISO4) | $S_T$ (mg/ml) | $\pi$ (atm) | $\pi \cdot S_d/100$ |
|---|---|---|---|---|
| 0 | 270 | 273 | 30 | 81 |
| 14.3 | 281 | 336 | 85 | 239 |
| 26.3 | 280 | 370 | 134 | 375 |
| 38.4 | 302 | 426 | 207 | 625 |
| 47.7 | 235 | 368 | 220 | 517 |
| 62.8 | 103 | 318 | 227 | 234 |
| 85.2 | 42 | 317 | 297 | 125 |
| 100.0 | 11 | 340 | 393 | 43 |

$\pi$ = OSMOTIC PRESSURE GENERATED FROM THE MIXTURE OF SALBUTAMOL HEMISULPHATE AND NaCl SOLUTION

COMPOSITION COMPRISING SALBUTAMOL

CROSS-REFERENCE TO COPENDING APPLICATIONS

This application is a division application of U.S. patent application Ser. No. 06/556,985 filed Dec. 1, 1983, now abandoned, and this application is copending with U.S. patent application identified by Ser. No. 07/001,599, filed concurrently herewith. These applications are assigned to ALZA Corporation of Palo Alto, Calif. and benefit is claimed of the filing date.

FIELD OF THE INVENTION

This invention pertains to an osmotic delivery system. More particularly, the invention relates to an osmotic system that delivers a beneficial agent (1) at a modulated pulsed rate followed by a substantially constant state, (2) at a substantially constant rate interrupted by a time related pulsed delivery of an increased amount of beneficial agent, (3) at a substantially constant rate followed by a terminal pulsed delivery of an increased amount of beneficial agent, or (and) a terminal pulse followed by a substantially zero order delivery period from the osmotic system.

BACKGROUND OF THE INVENTION

Osmotic delivery systems, manufactured as an osmotic delivery device, for delivering useful agents are becoming increasingly important articles of commerce and manufacture. These osmotic devices enjoy a wide application in the pharmaceutical, veterinary, husbandry and agriculture industries. The osmotic devices used by these industries exhibit a beneficial agent release rate that is substantially constant, once thermodynamic steady state conditions are established by the osmotic device. If the thermodynamic activity of the beneficial agent is maintained substantially constant in the device, then a steady state will be established with the release rate of agent from the device being constant over a prolonged period of time. This is commonly referred to as zero order release, a phrase suggested by physical-chemical kinetics.

The above described osmotic systems represent an outstanding advancement in the zero order delivery art for dispensing a beneficial agent continuously and at a constantly controlled rate. Now, it has been unexpectedly discovered a therapeutic result can be effected by a pulse dose of agent delivery. For example, estradiol administered at a low pulsed dose inhibits gonada-tropin secretion, while at high pulsed doses estradiol stimulates the ovulating surge of gonadotropin secretion, as reported in *Drugs,* Vol. 23, pages 207–226, 1982. Other therapeutic agents that produce a beneficial medical effect in this manner are pulsed methylprednisolone treatment of collagenic and progressing glomerulonephritis; pulsed cyclophosphamide-vincristine-adriamycin to patients suffering with neuroblastoma; pulsed rifampicin therapy in leprosy; pulsed oxytocin in the induction of labor; and pulsed insulin for the control of hyperglycemia; as reported in *Fertil. and Steril.,* Vol. 39, pages 695–699, 1983; *Vutr. Boles,* Vol. 21, pages 65–74, 1982; *Br. J. Cancer,* Vol. 45, pages 86–94, 1982; *Fert. and Steril.,* Vol. 36, pages 553–559, 1981; *Int. J. Radiat. Oncol. Biol. Phys.,* Vol. 8, pages 915–919, 1982; *J. Clin. Endocrinol. Metab.,* Vol. 53, pages 184–91, 1981; and, *Diabetes,* Vol. 26, pages 571–581, 1977.

Heretobefore, the prior art lacked a delivery system for administering a useful agent at a pulsed rate, particularly at a pulsed rate joined with a zero order rate of delivery. Thus, in the light of the above presentation, it will be readily appreciated by those versed in the dispensing art, that a critical need exists for a delivery system that can deliver a useful agent at a substantial zero order rate which is (a) preceeded by a pulsed delivery of the useful agent, (b) interrupted by a pulsed delivery of the agent, (c) terminated by a pulsed delivery of the agent, or (d) is a terminal pulse followed by a substantially constant delivery from the osmotic system. It will be further appreciated by those versed in the art, that it is a novel and useful device made available for delivering an agent at a constant rate and pulsed rate, such a device would have a positive value and also represent a valuable contribution to the dispensing art.

OBJECTS OF THE INVENTION

Accordingly, in the light of the above presentation, it becomes an immediate object of this invention to provide a novel and useful delivery device that can deliver a useful agent at a controlled rate accompanied by a timed pulsed delivery of an increased amount of useful agent.

Another object of the invention is to provide an osmotic delivery system that can deliver a beneficial drug at a controlled and constant rate with a time dependent pulsed delivery occurring when thermodynamic conditions have been established in the osmotic delivery system for effecting the pulsed delivery of the useful agent.

Yet another object of the invention is to provide more effective drug therapy by making available an osmotic delivery system for achieving maximum therapeutic action by delivering a drug at controlled rate at a constant concentration for a specific period that is accompanied by a concomitant pulsed delivery of drug for achieving optimum drug benefits.

Yet another object of the invention is to provide an osmotic drug delivery system that administers a drug concentration within an effective therapeutic range for the minimum period needed for treatment followed by the drug released in a pulsed dose needed for the final therapeutic treatment.

Yet another object of the invention is to provide an osmotic delivery system that administers a useful agent at a pulsed rate followed by a substantially zero order rate of useful agent delivery over a prolonged period of time.

Still yet another object of the invention is to provide an osmotic delivery system having modes of administration comprising steady drug delivery with a pulsed frequency of drug delivery, which system can be used in a method for dispensing a drug as a complete pharmaceutical regimen to a human, the use of which requires intervention only for initiation, and optionally termination of the regime.

Yet still another object of the invention is to provide an osmotic delivery system that dispenses a useful agent having terminal pulse followed by a substantially zero order delivery period of useful agent from the osmotic system.

Yet still another object of the invention is to provide an osmotic delivery system characterized by zero order drug release with a late drug delivery in an amount greater than the amount delivered at zero order release from the device, for supplying an increased amount of drug to a patient requiring more drug at a particular time of the day or night to maintain proper therapeutic efficacy.

Another object is to provide zero order delivery of useful agent followed by a useful agent pulse at the end of the regimen in order to increase the extent of absorption from the dosage form.

Other objects, features and advantages of the invention will be more apparent to those skilled in the dispensing art from a reading of the detailed description of the specification, taken in conjunction with the claims.

DETAILED DESCRIPTION OF THE INVENTION

This invention resides in the unexpected discovery that an osmotic delivery systems can be provided having a modulated release kinetic pattern. The invention provides an osmotic system that delivers a useful agent at a substantial zero order rate of release for a given period of time, modulated by a time dependent pulsed delivery of a greater than zero order amount of useful agent delivered from the osmotic system. The zero order pattern can be modulated by a pulse that precedes the zero order pattern, or by a zero order pattern modulated by a pulsed delivery that interrupts the zero order, or a modulated pulse can occur at the end of the zero order delivery or by a terminal pulse followed by zero order delivery. The unique release kinetics are achieved by charging the osmotic system with the useful agent and a modulating agent. The modulating agent is present in an amount such that it is the first of the two agents to fall below saturation in the osmotic system. When this occurs, the useful agent solubility increases and concomitantly the amount of useful agent released increases, giving the pulsed release for the system.

The useful agent and the modulating agent are delivered by an osmotic system manufactured as an osmotic device. The osmotic device comprises a wall that surrounds and defines a compartment. The compartment contains both a dosage unit amount of a beneficial agent and an effective amount of a modulating agent. The compartment optionally contains dispensing ingredients used for easy manufacture and controlled delivery. A passageway in the wall connects the compartment with the exterior of the osmotic device for delivering the useful agent from the osmotic device.

The wall of the osmotic delivery device is formed of a semipermeable composition that does not adversely affect the useful agent, the modulating agent, and the environment of use. The wall is formed of a semipermeable composition that is permeable to the passage of an external fluid, such as water and biological fluids, and it is impermeable to the passage of useful agent, the modulating agent and other ingredients present in the compartment. The selectively permeable polymers useful for manufacturing the osmotic device are represented by a member selected from the group consisting essentially of a cellulose ester, cellulose diester, cellulose triester, cellulose ether, cellulose ester-ether, cellulose acylate, cellulose diacylate, cellulose triacylate, cellulose acetate, cellulose diacetate, cellulose triacetate, cellulose acetate propionate, and cellulose acetate butyrate. Suitable semipermeable polymers useful for manufacturing osmotic devices are disclosed in U.S. Pat. Nos. 3,845,770; 3,916,899; 4,008,719; 4,036,228; and 4,111,210. These patents are assigned to the ALZA Corporation of Palo Alto, Calif., the assignee of this patent application.

In an embodiment, the wall of osmotic device can be a laminate comprising a semipermeable lamina in laminar arrangement with a microporous lamina. The semipermeable lamina is formed of the above polymers. The microporous lamina comprises a plurality of micropores and interconnected micropaths for admitting external fluid into the osmotic device. The microporous lamina can comprise the above polymers additionally housing a pore former that is dissolved, or leached from the lamina, when the osmotic device is in dispensing operation in the biological fluid environment of use. The pore formers are non-toxic, and they do not react with the materials forming the microporous lamina. On their removal from the lamina, the paths formed fill with fluid, and these paths become a means for fluid to enter the osmotic device, acting in cooperation with the semipermeable lamina. Typical pore formers are represented by sodium chloride, potassium chloride, sorbitol, mannitol, polyethylene glycol, hydroxypropyl methylcellulose, and hydroxypropyl butylcellulose. Osmotic dispensing devices having a laminated wall comprising a semipermeable lamina and a microporous lamina are disclosed in U.S. Pat. No. 4,160,452, assigned to the ALZA Corporation. The osmotic device in another embodiment can be coated on its exterior surface with a coating containing a dye. The coating is non-toxic and water soluble, containing a non-toxic dye. The coating can be on the semipermeable wall, or it can be on the laminated wall. For example, the coating can comprise hydroxypropyl methylcellulose mixed with Food, Drug and Cosmetic pharmaceutically acceptable lake dye.

The expression passageway as used herein for an osmotic device includes an aperture, orifice, bore, hole and the like embracing osmotic dimensions through the wall. The expression also includes an erodible element in the wall, such as a gelatin plug that erodes and forms an osmotic passageway in the environment of use. A detailed description of osmotic passageways, and the maximum and minimum dimensions for osmotic passageways are disclosed in U.S. Pat. Nos. 3,845,770 and 3,916,899. These patents are assigned to the ALZA Corporation.

The compartment of the osmotic device contains the useful agent and the modulating agent present in nonequilibrium proportions. Prior to this invention, the compartment contained, for example, a useful agent and an osmotic agent present in ratio, which represented the ratio of mutual solubility between the two components in the compartment. In this invention, the useful agent and the modulating agent are present in a nonequilibrium ratio. The modulating agent, which acts as a suppressant optionally termed a desolubilizer for the useful agent, is used initially in an amount sufficient for it to be the first of the two agents to fall below saturation. Concurrent with this thermodynamic result, the solubility of the useful agent is enhanced, thereby increasing the amount of useful agent released at the pulsed moment.

Figure 1A:
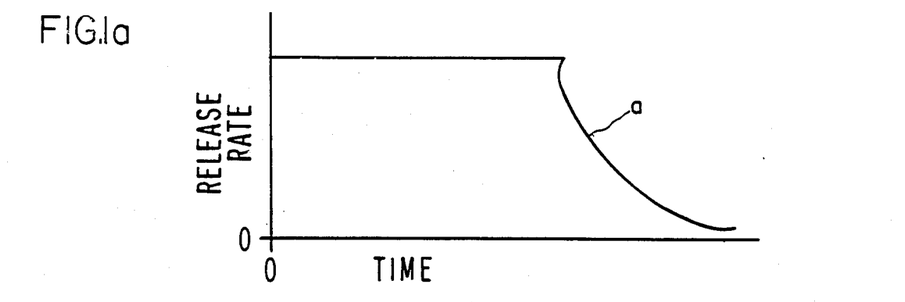
Figure 1B:
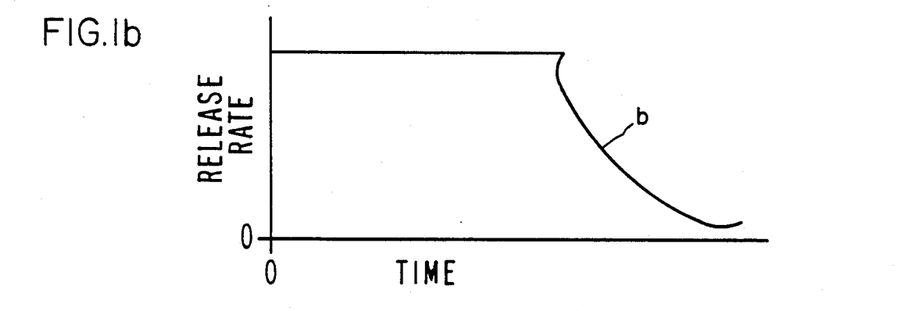

The solubility of the useful agent is lowered when cosolubilized with a modulating agent. More specifically, the process occurs in the presence of fluid imbibed through the semipermeable wall into the compartment, whereby in the presence of the imbibed fluid the modulating agent diminishes the solubility of the useful agent. In conventional cosolubilization, the useful agent and the osmotic agent are present in an equilibrium ratio, and the release rate profile follows the traditional pattern as seen in FIG. 1a and FIG. 1b. In FIGS.

Figure 2A:
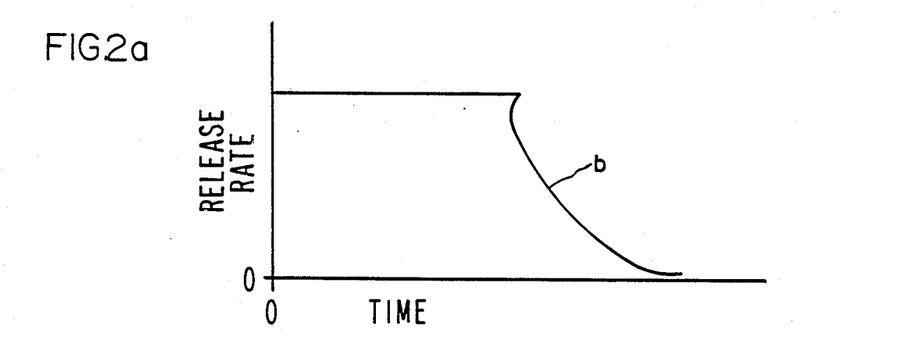
Figure 2B:
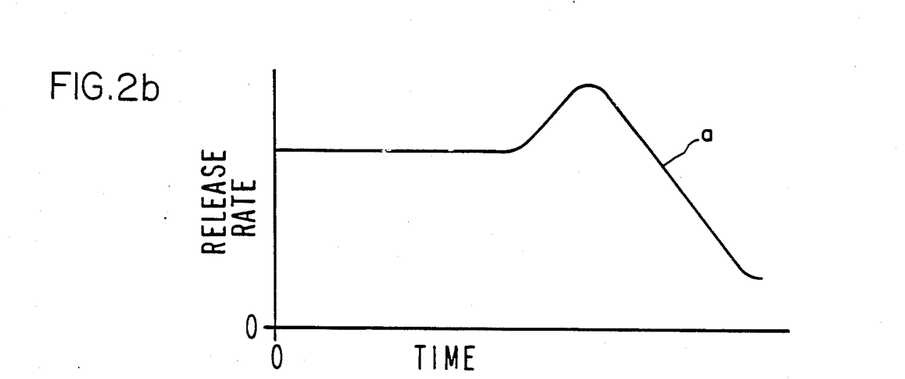
Figure 3A:
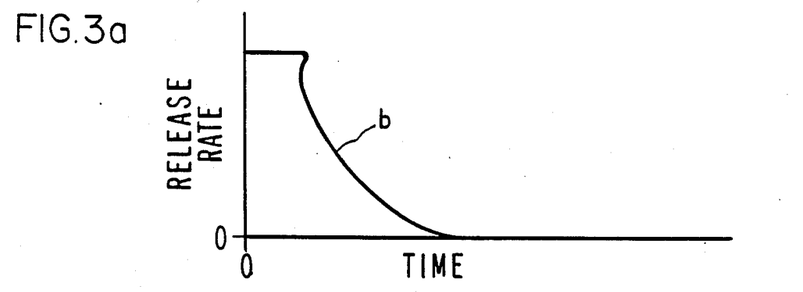
Figure 3B:
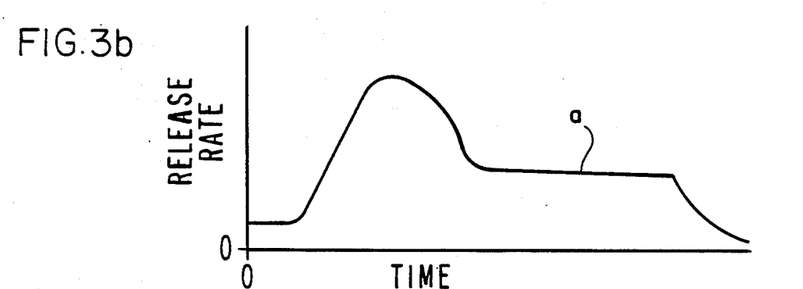

1a and 1b, the release rate profile for both the useful agent, line a, and the modulating agent, line b, are linear over time, and then both decline in a like manner as the concentration of both a and b fall below saturation in the fluid in the compartment. In this invention, cosolubilization of the useful agent and the modulating agent are exemplified by a nonequilibrium ratio, and the release rate profile is depicted in FIG. 2a and 2b. In FIG. 2a, the concentration of the modulating agent b, is below the equilibrium ratio in the compartment, and it is exhausted at an earlier time than the exhaustion of the useful agent a. Consequently, there is a drastic increase in the solubility of the useful agent a, in the less than saturated modulating agent solution, and the release rate for the useful agent is actually increased as seen by curve a in FIG. 2b. A further reduction of the concentration of the modulating agent will result in the pair of release rate profiles illustrated in FIG. 3a and FIG. 3b. FIG. 3a illustrates the release rate profile for the reduced modulating agent b concentration, and FIG. 3b illustrates the delay release of useful agent a resulting from the reduction of the concentration of the modulating agent. In the light of this presentation, it becomes evident this invention provides both an osmotic system and a method for preprogramming to a desired time of release, a delayed release, or a delayed pulsed release of useful agent, that in either instance is achieved by adjusting the conentration of the modulating agent in the osmotic system.

The timing of the pulsed delivery of useful agent is a function of the amount of modulating agent and the properties of the osmotic system. The timing of the pulsed release to start is represented by the following formula:

$$T = \frac{M_o \cdot h \cdot (1 - S_t/p)}{S_o \cdot \Delta \pi_t \cdot KA}$$

wherein T is the time of beginning of pulsed delivery; $M_o$ is the weight of the modulating agent present in the osmotic device initially; h is the thickness of the semipermeable wall; $S_t$ is the total solubility of both the modulating agent and the useful agent in the osmotic device; $p$ is the density of the total mass in the osmotic device; $S_o$ is the mutual solubility of the modulating agent in aqueous media; $\Delta \pi_t$ is the total osmotic pressure generated by of both the modulating agent and the useful agent in the osmotic device; K is the permeability of the semipermeable wall; and A is the total surface area of the compacted mass present in the compartment of the osmotic device.

The expression useful agent as used herein denotes an algicide, air purifier, anti-oxidant, biocide, catalysts, chemical reactant, cosmetic, drug, disinfectant, fungicide, fermentation agent, food, food supplement, fertility inhibitor, fertility promotor, germicide, herbicide, insecticide, micro-organism attenuator, nutrient, pesticide, plant growth promotor, plant growth inhibitor, preservative, sex sterilant, sterilization agent, vitamin, and other useful agents that benefit the environment of use.

In the specification and the accompanying claims, the term drug includes any physiologically or pharmacologically active substance that produces a localized or systemic effect in animals, including warm blooded animals, mammals, humans, primates, avians, reptiles, and pisces. The term animals also includes domestic household animals, sport and farm animals, such as sheep, goats, cattle, horses, and pigs, and for administering to laboratory animals, jungle animals and zoo animals. The active drug can include inorganic and organic compounds without limitation, those materials that act on the central nervous system such as hypnotics and sedatives, psychic energizers, tranquilizers, antidepressants, anticonvulsants, muscle relaxants, antiparkinson, analgesic, anti-inflammatory, anesthetic, muscle contractant, anti-infective, anti-microbial, anti-malarial, hormonal agents, sympathomimetic, metabolic aberration correcting agents, diuretics, anti-parasitic, neoplastic, hypoglycemic, nutritional, fat, ophthalmic, elutrolyte, cardiac and diagnostic agents. The drugs act on the peripheral nerves, adrenergic receptors, cholinergic receptors, nervous system, skeletal muscles, cardiovascular, smooth muscles, blood circulatory system, synoptic sites, neuroeffector junctional sites, endocrine and hormone systems, immunological system, reproductive system, skeletal system, autocoid system, alimentary and excretory system, inhibitory of autacoids and histamine systems, and system that acts on all sites of the central nervous system. The amount of useful agent present in an osmotic system is generally for a drug dosage unit amount to give the desired therapeutic effect. Generally, the osmotic system can house from 0.05 ng to 5 g or more, with individual systems containing for example, 25 ng, 1 mg, 5 mg, 50 mg, 100 mg, 125 mg, 250 mg, 500 mg, 750 mg, 1.5 g and the like.

The modulating agents useful for the purpose of this invention are soluble in aqueous and biological fluids, such as ionizing compounds, inherently polar compounds, inorganic acids, organic acids, bases and salts, and salts containing a common ion with the drug. In a preferred embodiment the compounds are solids and they dissolve and form a solution with fluids imbibed into the osmotic device. Examplary inorganic salts are represented by a member selected from the group consisting essentially of lithium chloride, lithium sulfate, magnesium chloride, magnesium sulfate, potassium chloride, potassium sulfate, potassium acid phosphate, sodium chloride, sodium sulfate, sodium sulfite, sodium nitrate, sodium nitrite, and the like. Salts of organic acids are represented by a member selected from the group consisting essentially of sodium citrate, potassium acid tartrate, potassium bitartrate, sodium bitartrate, and the like. Representative of a therapeutically acceptable salt having a common ion effect with a useful agent or drug is sodium chloride and sodium indomethacin; triflupromazine hydrochloride and sodium chloride; or phenelzine sulfate and sodium sulfate. The ionizable solid acids useful as modulating agents are represented by a member selected from the group consisting essentially of tartaric, citric, maleic, malic, fumaric, tartronic, itaconic, adipic, succinic, mesaconic acid, and the like. The basic compounds are represented by a member selected from the group consisting essentially of potassium carbonate, sodium carbonate, ammonium carbonate, and the like.

Figure 4A:
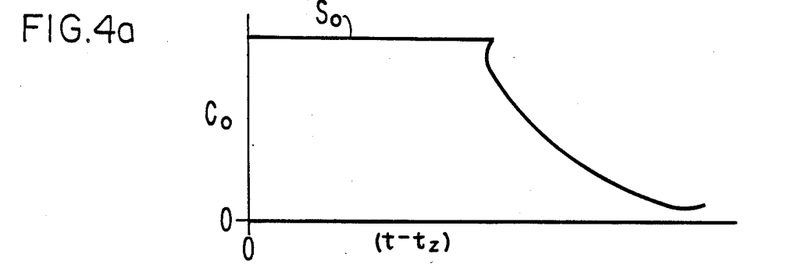

The concentration of the modulating agent inside the osmotic system during its non-zero order period from an osmotic device is given by equation 1.

$$C_0 = \frac{V_t S_o}{V_t + \frac{Z_o}{S_o}(t - t_z)} \qquad (1)$$

wherein $C_o$ is the concentration of modulating agent in the osmotic device during its non-zero order period, $V_t$ is the total internal volume of the osmotic device, $Z_o$ is the zero order release rate of the modulating agent, $S_o$ is the solubility of the modulating agent, t is the time at the start of the delivery, and $t_z$ is the zero order delivery time of the modulating agent. The release rate pattern for the modulating agent of equation 1 is depicted in FIG. 4a.

Figure 4B:
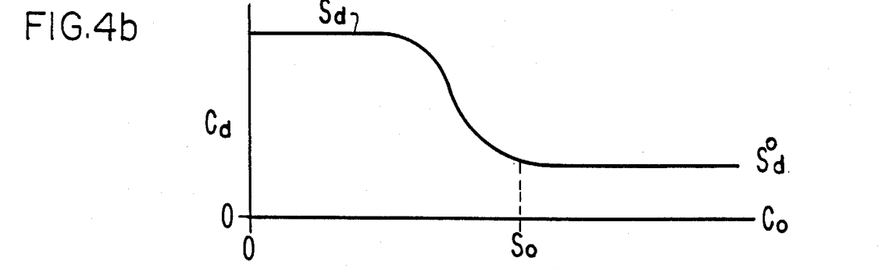
Figure 14:
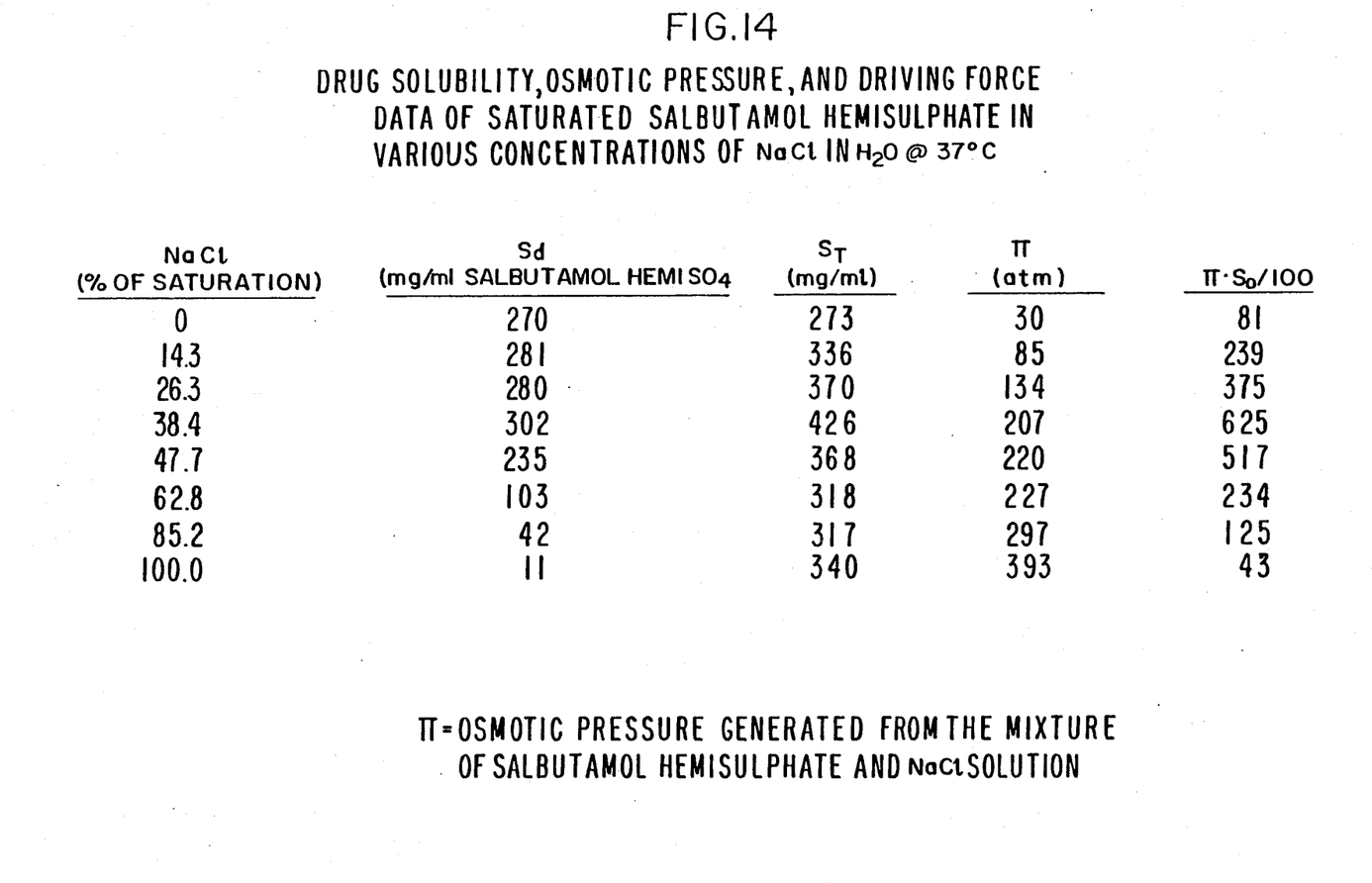

Conversely, the solubility of the useful agent increases with the decrease of the modulating agent concentration such that as the concentration of the modulating agent $C_o$ approaches zero, $C_o \to O$, the concentration of the useful agent Cd inside the osmotic system equals the solubility of the useful agent Sd in water, Cd=Sd at large value. Also, when the concentration of the modulating agent $C_o$ equals the saturated solubility $S_o$ of the modulating agent, the concentration of the useful agent Cd equals the concentration of the mutual solubility of the useful agent and the modulating agent, $Cd = S°d$ at small value, as depicted by FIG. 4b. The Table shown in FIG. 14 lists experimental data of the solubility of a useful agent, salbutamol, in different concentrations of modulating agent, NaCl.

The concentration of useful agent decreases nomotonically between these two limits as the modulating agent's concentration is exhausted over time. The useful agent rate of release from the osmotic device is represented by equation 2.

$$\left(\frac{dm}{dt}\right)_d = \frac{A}{(h)} k\pi_t Cd \quad (2)$$

wherein (dm/dt)d is the release rate of the useful agent, k is the water permeability of the semipermeable membrane, A is the surface area of the osmotic device, h is the thickness of the semipermeable membrane, Cd is the concentration of useful agent in the osmotic device, and it is the osmotic pressure generated by the formulation consisting of useful agent and modulating agent.

Figure 4C:
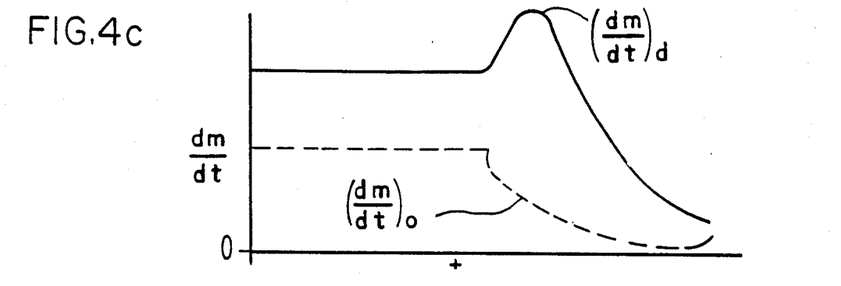

Thus, as $C_o$ continually diminishes according to equation 1, $C_d$ increases from a small value $S°_d$ to a large value $S_d$ thus resulting in a large increase in $(dm/dt)_d$ according to equation 2, accompanied by a pulse in the release profile as seen in FIG. 4c, wherein (dm/dt)o is the release rate of the modulating agent. In the osmotic device, the total driving force for the drug delivery is the product of $\pi_t C_d$. The $\pi_t C_d$ is maximum at certain concentration of the modulating agent. In the example given in Table I, the peak of the pulse occurs at about $C_o/S_o \approx 0.38$. Accordingly, the ratio of modulating agent to useful agent, R, can be any value $O<R<(S_o/S_d)$ in which $S_o/S_d$ is the mutual solubility of the useful agent in the modulating agent.

The useful agent and the modulating agent can be present in the compartment mixed with a binder, dye, lubricant, dispersant, and like pharmaceutical compounding ingredients. The pharmaceutical compounding ingredients include binders such as poly(ethylene glycol), gelatin, agar, carboxycellulose, poly(vinyl alcohol), and poly(vinyl pyrrolidone). Typical lubricants include stearic acid, magnesium stearate, zinc stearate, aluminum stearate, halogenated vegetable oil, and talc. The compartment can contain also a disintegrant to effect dissolution and solution forming of the useful agent and the modulating agent, for enhancing controlled delivery from the osmotic device. Typical disintegrants include lightly cross-linked poly(vinyl pyrrolidone), corn starch, potato starch, Veegum, bentonite, and citrus pulp. The coloring agents include Food, Drug and Cosmetic approved non-toxic dyes such as blue number 1 in lactose. Optionally, the dye in the compartment, and a dye in the wall can be the same dye or a different dye. The amount of a binder, a lubricant, or a disintegrant usually is about 0.01% to 20% respectively of the total weight present in the compartment.

The osmotic systems provided by this invention containing the useful agent, the modulating agent and other ingredients are manufactured by standard manufacturing techniques. For example, in one embodiment the useful agent is mixed in a nonequilibrium ratio with the modulating agent, and other compartment core ingredients by balling, calendering, stirring, and pressing the ingredients into a preselected shape corresponding to the shape of the final osmotic device. The material forming the wall of the device can be applied by dipping, molding or spraying the pressed blend. One procedure for applying the semipermeable wall, or the laminated wall is the air suspension technique. This technique can be used for manufacturing a wall formed of a single layer, or for forming a laminated wall formed of two layers. The air suspension procedure is described in U.S. Pat. No. 2,799,241; in *J. Am. Pharm. Assoc.*, Vol. 48, pgs. 451 to 459, 1959; and in ibid, Vol. 49, pgs. 82 to 84, 1960. An osmotic passageway is made by mechanical drilling, laser drilling, punching or cutting with a die. A procedure for forming the passageway using a laser is described in U.S. Pat. Nos. 3,916,899; and in 4,088,864, both assigned to the ALZA Corporation. The osmotic delivery device designed for oral administration can embrace various conventional shapes and sizes such as round with a diameter of 3/16 inches to 9/16 inches, or it can be shaped like a solid capsule having a range of sizes from triple zero to zero, and from 1 to 8. In these forms, the osmotic device is sized, shaped, structured and adapted for administering the useful agent to warm-blooded animals, which includes humans. Other standard manufacturing procedures are described in *Modern Plastic Encyclopedia*, Vol. 46, pgs. 62 to 80, 1969; in *Remington's Pharmaceutical Sciences*, 14th Ed., pgs. 1649 to 1698; and in *The Therapy and Practice of K. Industrial Pharmacy*, by Lackmann et al., pgs. 197 to 225, 1970.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the dispensing art in the light of the present disclosure and the accompanying claims.

EXAMPLE 1

An osmotic therapeutic device for the controlled delivery of the β-adrenergic stimulant and bronchodilator salbutamol, or α-[(tertbutylamino)methyl]-4-hydroxy-m-xylene-α,α'-diol-hemisulfate, delivered at a constant rate modulated by a pulsed rate is made as follows: first, the solubility of salbutamol hemisulfate (hereafter salbutamol) and the modulating agent sodium chloride were measured in distilled water at 37° C. and the measurements indicated the following solubilities:

solubility of salbutamol in water is 275 mg/ml, solubility of salbutamol in saturated solution of sodium chloride is 16 mg/ml, solubility of sodium chloride water is 321 mg/ml, solubility of sodium chloride in saturated solution of salbutamol is 320 mg/ml, and, the total solubility of salbutamol in saturated sodium chloride and sodium chloride in water is 16 plus 320 equal to 336 mg/ml.

Next, a composition is prepared containing salbutamol and sodium chloride in a ratio of 1:5 as follows: first, 14.45 mg of salbutamol, 72.30 mg of sodium chloride, 1.8 mg of cross-linked sodium carboxymethylcellulose, and 1.8 mg of poly(vinyl pyrrolidone) are passed through a 60 mesh screen and mixed in a blender for 1 hour. Then, the blended ingredients are transferred to a larger blender and 8 ml of a granulating fluid consisting of ethanol:water, 90:10, is added thereto and all the ingredients blended for about 20 minutes. The homogenously blended ingredients next are passed through a 20 mesh screen and dried in a forced air oven at 50° C. for 12 hours. After drying, the granules are mixed with 0.9 mg of magnesium stearate and blended for 10 minutes. The granules are transferred to a conventional Manesty tablet press and compressed with a standard round 5/32 inch dye to a hardness of 1.5 to 2 Kp. The area of the compressed drug core measured 0.41 $cm^2$ and weighed 91.3 mg.

The compressed core is transferred to an Aeromatic ® air suspension coater, and a wall consisting of cellulose acetate having an acetyl content is coated around the core. The semipermeable wall is formed from a composition comprising 42.5% (12.75 g) of cellulose acetate having an acetyl content of 39.8%, 42.5% (12.75 g) of cellulose acetate having an acetyl content of 32.0%, 15% (4.5g) of hydroxypropyl methyl cellulose in a cosolvent consisting of methylene chloride-methanol, 80%-20% (588 ml-256 ml). After the wall is formed around the reservoir, they are transferred to a forced air oven and air dried for 48 hours at 50° C. Next, an osmotic passageway having a diameter of 0.25 mm is laser drilled through the semipermeable wall. The semipermeable wall weight is 5.9 mg.

Figure 5:
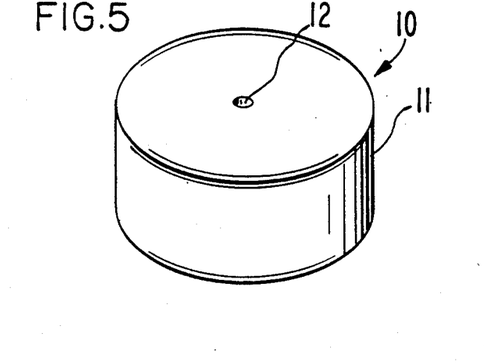
Figure 6:
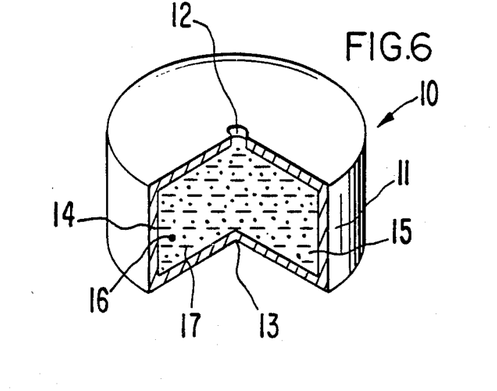
Figure 7:
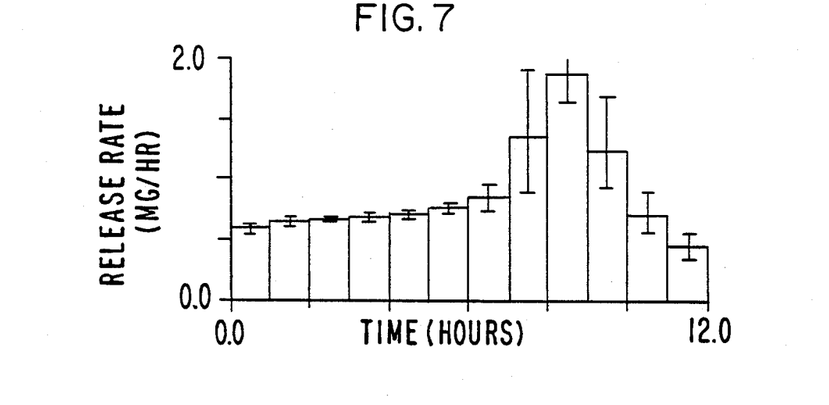
Figure 8:
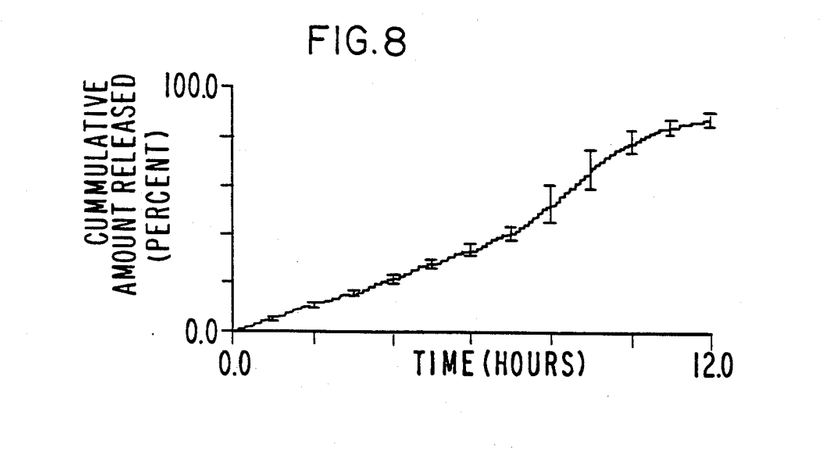

The osmotic useful agent delivery device prepared by the example is illustrated in FIGS. 5 and 6. In FIG. 5, the osmotic device 10 is seen comprising a body 11 with a passageway 12 that connects the exterior with the interior of osmotic device 10. In FIG. 6, osmotic device 10 is seen in opened section at 13 and it comprises semipermeable wall 14 that surrounds and defines internal compartment 15. Compartment 15 contains useful drug salbutamol 16, modulating agent sodium chloride 17, and other dispensing ingredients. In FIG. 7, the release rate pattern for the device is seen consisting of an essentially zero order rate of release for 7 hours, modulated by a pulsed release of useful agent from 7 to 9 hours. FIG. 8 depicts the cumulative amount of useful agent salbutamol delivered over a 12 hour delivery period. In the FIGS. 7 and 8, the bars represent the maximum and the minimum rate of release at the time of measurement.

EXAMPLE 2

An oral, osmotic device for the controlled codelivery of salbutamol and the bronchodilator terbutaline sulfate, 1-(3,5-dihy- droxyphenyl)-2- (tert-butylamino) ethanol, at a constant rate interrupted by a pulsed rate delivery is made as follows: first, 9.64 mg of salbutamol 5 mg of terbutaline sulfate, 24 mg of sodium chloride, 0.71 mg of poly (vinyl pyrrolidone), and 0.71 mg of cross-linked sodium carboxymethyl cellulose are blended and passed through a 60 mesh screen. The ratio of the salbutamol to sodium chloride in the composition is 1 to 3. Next, 8 ml of a granulating fluid consisting of ethanol:water, 90:10, is added to the screened blend, and all the ingredients blended for about 15 to 20 minutes. The well-blended ingredients are passed through a 30 mesh screen and dried in a forced air oven for 12 to 15 hours at 50° C. After drying, the granules are mixed with 0.35 mg of stearic acid and blended for 10 minutes. Then, the blend is compressed into a precompartment forming drug formulation. The compressed drug formulation is placed in an air suspension machine and coated with a microporous lamina forming composition. The microporous lamina composition comprises 49% by weight of cellulose acetate having an acetyl content of 39.8%, 28.5% by weight of hydroxypropyl methylcellulose, and 22.5% by weight of polyethylene glycol 4000. The lamina is formed from a methylene chloride-ethanol (95%) lamina solvent (80:20 wt:wt). The microporous lamina is 0.12 mm thick.

Figure 9:
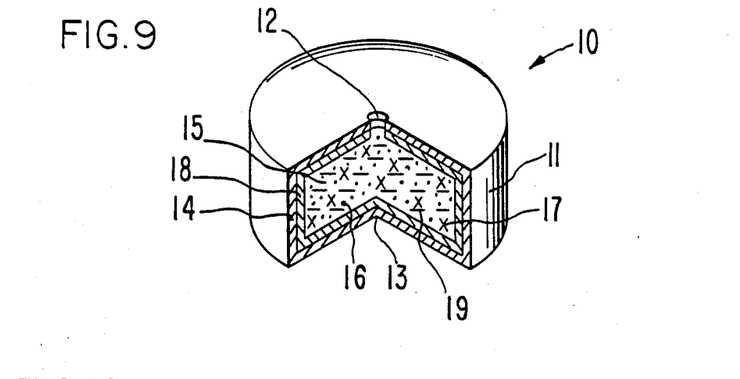

Next, an exterior semipermeable lamina is laminated onto the microporous lamina in the conventional air suspension machine. The semipermeable lamina forming composition comprises 90% by weight of cellulose acetate having an acetyl content of 39.8% and 10% cellulose acetate having an acetyl content of 32%. The semipermeable lamina is applied in laminar arrangement from a solvent mixture comprising methylene chloride and ethanol (80:20 wt:wt). The osmotic devices are dried and a passageway having a diameter of 0.26 mm is drilled with a laser through the laminated wall. In FIG. 9, osmotic device 10 is seen comprising body 11, passageway 12, opened section 13, outside semipermeable wall 14, inside compartment 15, salbutamol 16, sodium chloride 17, inside microporous wall 18 and terbutaline 19.

EXAMPLE 3

An oral, osmotic device for the controlled and continuous delivery of oxprenolol-HCl modulated by a pulsed release of oxprenolol-HCl is made by following the general procedure described about. In the osmotic device of this example, the compartment houses a drug formulation comprising a nonequilibrium formulation of 1 part of oxprenolol-HCl to 6 parts of potassium chloride:sodium chloride (50:50) mixture. The compartment contains also 2 mg of dextrose, 2 mg of potato starch and 3 mg of magnesium stearate. The formulation after compressing has a diameter of 9 mm. The device has a laminated wall consisting essentially of 60% by weight of cellulose acetate having an acetyl content of 43.5% and a degree of substitution of 3 and 40% by weight of cellulose acetate having an acetyl content of 39.8 and a degree of substitution of 2.4. The semipermeable lamina is applied from a solvent consisting essentially of methylene chloride and methanol, 80:20by weight. The device has an exterior microporous lamina consisting essentially of 55% by weight of cellulose acetate having an acetyl content of 39.8%, 35% by weight of sorbitol, and 10% by weight of polyethylene glycol 400. The lamina is applied from a solvent comprising methylene chloride-methanol, 90:10 by weight. The semipermeable lamina is 0.12 mm thick, and the microporous lamina is 0.13 mm thick. The device has a 0.25 mm passageway.

EXAMPLE 4

Figure 10:
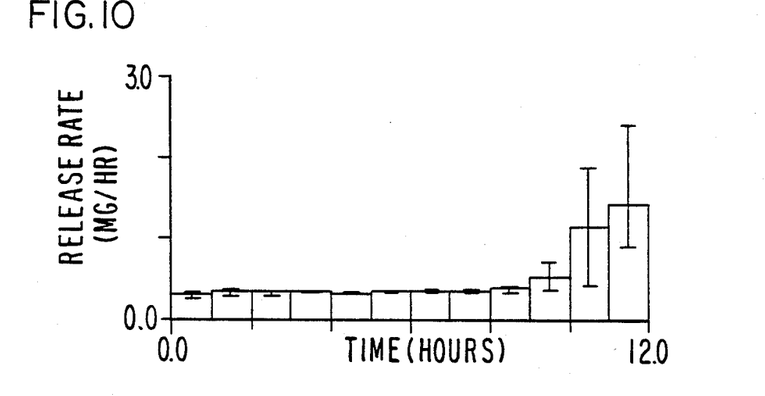

The procedure of Example 1 is repeated to yield an osmotic device wherein the ratio of salbutamol to sodium chloride is 1 to 7, and the compartment of the osmotic device contained a drug formulation consisting essentially of 9.6 mg of salbutamol hemisulfate, 56 mg of sodium chloride, 1.4 mg of poly(vinyl pyrrolidone), 1.4 mg of cross-linked sodium carboxymethyl cellulose and 0.6 mg of magnesium stearate. The device delivers salbutamol for 12 hours and has a terminal pulsed release of salbutamol as seen in FIG. 10. The osmotic device has a semipermeable wall 4.9 mils thick (0.13 mm), comprising the semipermeable wall composition of Example 1.

EXAMPLE 5

Figure 11:
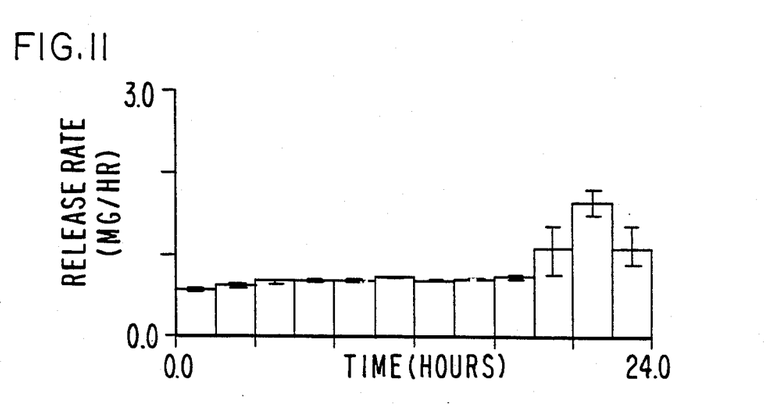

The procedure of Example 1 is followed to yield an osmotic device wherein the ratio of salbutamol to the modulating agent sodium chloride is 1 to 9. The compartment of the osmotic device contains a drug formulation consisting essentially of 28.9 mg of salbutamol hemisulfate, 216 mg of sodium chloride, 5.2 mg of poly(vinylpyrrolidone), 5.2 mg of cross-linked sodium carboxymethyl cellulose, and 2.6 mg of magnesium stearate. The osmotic device has a semipermeable wall weighing 20.1 mg comprising the composition of Example 1. The device has a zero order rate of release of salbutamol for 16 hours followed by an increased pulsed salbutamol for 8 hours. The 24 hour release pattern for the osmotic device is illustrated in FIG. 11.

EXAMPLE 6

An oral osmotic device that delivers acebutolol, a β-adrenergic blocker, is sized, shaped and manufactured for administration into the gastrointestional tract as follows: 10 parts of acebutolol hydrochloride and 90 parts of potassium carbonate, 8.75 mg of noncross-linked poly(vinylpyrrolidone) are mixed and passed through a 60 mesh stainless steel screen and blended for 1 hour at room temperature. Next, the blended ingredients are transferred to a larger blender and 40 ml of a granulating fluid consisting of ethanol:water, 90:10 by volume, is added to the blender, and the ingredients blended for 20 minutes. The thoroughly blended ingredients are passed through a 30 mesh screen and dried in a forced air oven at 50° C. for 16 to 17 hours.

Then, the dried granules are passed through a 20 mesh screen and 5 mg of magnesium stearate is added to the granules. The ingredients are blended for 15 minutes, and the blended granules transferred to a conventional Manesty press. The ingredients are compressed into acebutolol reservoirs having a diameter of about 6 mm.

The acebutolol precompartment forming compositions are transferred to an air suspension coater and surrounded with a semipermeable wall. The semipermeable wall is formed from a wall forming composition comprising 35 g of cellulose acetate having an acetyl content of 39.8 from an organic solvent consisting essentially of 550 ml of methylene chloride and 110 of methanol. After the semipermeable wall is formed surrounding the drug reservoir, they are dried in a forced air oven for 50 hours at 50° C. Next, a 0.4 mm passageway is laser drilled through the semipermeable wall connecting the interior compartment with the exterior of the osmotic device. The semipermeable wall weighed 8.6 mg and the device delivers the drug for 12 hours time span modulated by a terminal pulsed delivery.

EXAMPLE 7

Figure 12:
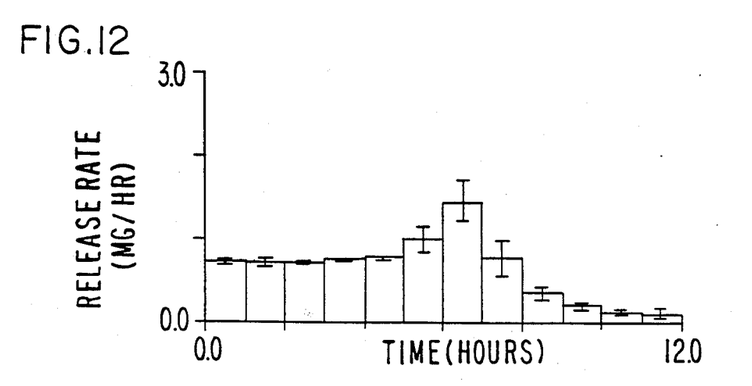
Figure 13:
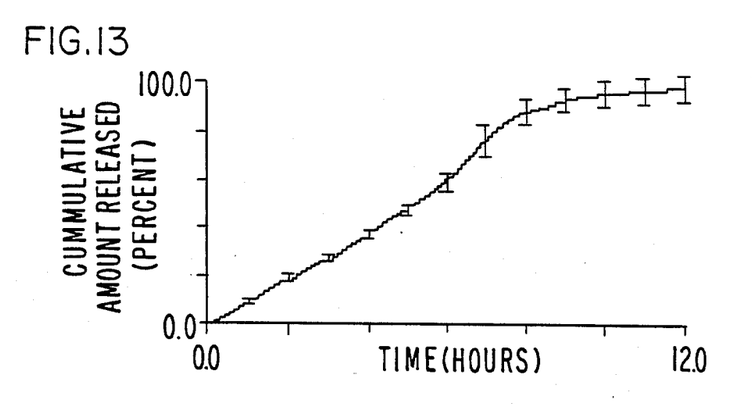

The procedure of Example 1 is repeated to manufacture an osmotic device wherein the ratio of useful agent salbutamol to modulating agent is 1 to 9 to produce a device wherein the pulsed delivery occurs near the middle of the release pattern. In Example 7, the osmotic device comprises 9.3% by weight of salbutamol, 1.9% by weight as the hemisulfate, 83.8% by weight of sodium chloride, 2% by weight of cross-linked sodium carboxymethyl cellulose, 2% by weight of polyvinylpyrrolidone, and 1% by weight of magensium stearate. The device has a semipermeable wall consisting of 42.5% by weight of cellulose acetate having an acetyl content of 39.8%, 42.5% by weight of cellulose acetate having an acetyl content of 32%, and 15% by weight of hydroxypropyl methylcellulose. The diameter of the passageway is 0.25 mm, the semipermeable wall weighs 4.8 mg and the wall is 0.06 mm thick. The measured release rate pattern for the osmotic device is depicted in FIG. 12 and the cumulative amount released is illustrated in FIG. 13.

The invention in one presently preferred embodiment pertains also to a method for delivering a drug at a constant rate modulated by a pulsed delivery of the drug, which method comprises the steps of: (A) admitting orally osmotic device shaped, sized and structured into the gastrointestional tract of a patient, the osmotic device comprising: (a) a wall formed of a nontoxic semipermeable composition that is permeable to the passage of an exterior fluid and substantially impermeable to the passage of drug and modulating agent, the wall surrounding and forming; (b) a compartment containing a dosage unit amount of drug and an effective amount of modulating agent which modulating agent is a means for providing a pulsed delivery of drug; and (c) a passageway in the wall for communicating the exterior of the osmotic device with the interior of the osmotic device; (B) imbibing exterior fluid through the semipermeable wall into the compartment at a rate determined by the permeability of the semipermeable wall and the osmotic pressure gradient across the semipermeable wall to form a solution comprising drug that is hydrodynamically and osmotically delivered from the osmotic device; and (C) delivering the drug in a therpeutically effective amount at a substantially constant rate accompanied by a pulsed delivery of drug in an effective amount larger than the constant rate through the passageway to the gastrointestinal tract of the patient to produce the desired beneficial effect of the constant rate and the pulsed rate of drug delivery over the prolonged period of time.

The osmotic devices also can be used as an implant, or a conduct can be attached to the passageway for intravenous delivery of drug, or for subcutaneous delivery of drug. Drugs that can be delivered in a zero order rate with a pulsed rate comprise a method for the controlled and substantially constant delivery of salbutamol accompanied by a pulsed delivery of salbutamol; a method for the controlled and constant delivery of acebutolol accompanied by a time-dependent pulsed delivery of acebutolol; a method for the management of asthma which method comprises administering to a patient suffering with asthma a therapeutically effective amount of salbutamol at a constant rate interrupted by a pulsed amount of salbutamol for producing a beneficial effect in said asthmatic patient. The salbutamol and acebutolol also can be administered in a method for producing bronchodilation in a patient in need of a bronchodilator, particularly for acute and chronic patients. The beneficial agent is delivered at a controlled and continuous rate over a period of time from 15 minutes to 24 hours accompanied by an intermittent pulsed or terminal pulsed delivery of 15 minutes to 24 hours.

The invention provides an osmotic therapeutic system manufactured in the form of an osmotic device for producing an improved drug delivery program. While there has been described and pointed out the novel features of the invention as applied to presently preferred embodiments, those skilled in the art will appreciate that various modifications, changes and omissions in the invention illustrated and described can be made without departing from the spirit of the invention.

We claim:

1. A composition for use in an osmotic device comprising: a beneficial agent comprising salbutamol, a modulating agent comprising sodium chloride which sodium chloride is present in an amount relative to the salbutamol less than the amount needed for the sodium chloride to maintain saturation in a fluid that enters the osmotic device, and wherein the composition when in said osmotic device is useful for dispensing salbutamol at a substantially zero order rate of delivery accompanied by a pulsed rate of delivery.

* * * * *